United States Patent [19]

Arnold et al.

[11] 4,455,439
[45] Jun. 19, 1984

[54] PROCESS FOR THE PREPARATION OF KETENE

[75] Inventors: Dieter Arnold, Königstein; Jörg Bartels, Eppstein; Heinrich Lenzmann, Kelkheim; Günter Jacobsen, Offenbach am Main; Heinz Wendt, Sulzbach; Manfred Stoltenberg, Frankfurt am Main, all of Fed. Rep. of Germany

[73] Assignee: Hoechst Aktiengesellschaft, Frankfurt am Main, Fed. Rep. of Germany

[21] Appl. No.: 327,510

[22] Filed: Dec. 4, 1981

[30] Foreign Application Priority Data

Dec. 8, 1980 [DE] Fed. Rep. of Germany ....... 3046219

[51] Int. Cl.$^3$ .............................................. C07C 45/51
[52] U.S. Cl. .................................................. 568/302
[58] Field of Search .......................................... 568/302

[56] References Cited

U.S. PATENT DOCUMENTS

| | | | |
|---|---|---|---|
| 2,816,143 | 12/1957 | Probst | 568/302 |
| 2,820,058 | 1/1958 | Luke et al. | 568/302 |
| 2,967,888 | 1/1961 | Altenschpfer et al. | 568/302 |
| 3,480,676 | 11/1909 | Scheuber | 568/302 |

FOREIGN PATENT DOCUMENTS 1643758 12/1970 Fed. Rep. of Germany ...... 568/302

OTHER PUBLICATIONS

Perry et al., "Chem. Engineers' Handbook", pp. 10-30 to 10-31, McGraw-Hill, (1979).

*Primary Examiner*—James H. Reamer
*Attorney, Agent, or Firm*—Curtis, Morris & Safford

[57] ABSTRACT

In this process for the preparation of ketene by the thermal, catalytic cracking of acetic acid under reduced pressure, the hot cracked gases are cooled to approx. 0° to $-10°$ C. and, in the course thereof, water, unreacted acetic acid and acetic anhydride are condensed. The quantity of acetic acid employed for the thermal cracking reaction should be 0.5 to 2.5 $t \times hours^{-1} \times m^{-3}$, relative to the volume V of a shell-and-tube heat exchanger through which the cracked gas is passed. The pressure drop in the tubular heat exchanger should be 50 to 150 mbars and the surface/volume ratio should be 60 to 120 $m^{-1}$.

4 Claims, No Drawings

PROCESS FOR THE PREPARATION OF KETENE

The invention relates to a process for the preparation of ketene by the thermal, catalytic cracking of acetic acid under reduced pressure and by cooling the hot cracked gases to approx. 0° C. to −10° C., in the course of which water, unreacted acetic acid and acetic anhydride are condensed.

In a known industrial process for the preparation of ketene, acetic acid is cracked continuously in the presence of, for example, triethyl phosphate as a catalyst at a temperature above 700° C. and under a pressure ranging from about 100 to 500 mbars. Ammonia is added to the hot cracked gas shortly after it leaves the reaction zone in order to bind phosphoric acid. Besides ketene and water, the cracked gas contains the following gases which originate from side reactions: methane, carbon dioxide, carbon monoxide, ethylene, allene and, in small quantities, higher hydrocarbons and also uncracked acetic acid and ammonium salts of acetic acid and phosphoric acid.

Ketene is isolated from the cracked gas by first cooling the latter as rapidly as possible, in order to remove the condensable constituents. In doing this, it is not possible to prevent the ketene from coming into contact with water and acetic acid and reacting, with the formation of acetic acid and acetic anhydride. A condensate composed of water, acetic acid and acetic anhydride is thus obtained in the cooling process. The undesirable consequence of this reaction, in which some of the ketene formed is re-converted into the starting material, is not only a decrease in the degree of conversion of the acetic acid, but also an increase in the energy requirement of the plant. Condensation in vacuo is incomplete even at low temperatures. The cracked gas still contains mists of acetic acid and acetic anhydride which are difficult to remove.

In the process disclosed in German Auslegeschrift 1,250,811, the cracked gas, which is at a temperature of approx. 700° C., is first cooled to 50° C. and is then passed over a cyclone separator and is cooled further. Any mist present is not removed in this process. The reverse reaction is considerable under these conditions, particularly in the case of plants having fairly large throughputs, and can be detected from the high concentration of acetic acid in the condensate.

It is known from German Patent Specification No. 1,643,758 to pre-cool the cracked gas initially to approx. 120° C., in order then to pass them through a perforated cooling section in which the condensate can flow away immediately, the cooling section being kept at a temperature of −20° to −30° C. by means of cooling brine. The crude ketene is then made to flow against baffles, in order to remove the mist of acetic acid and acetic anhydride. The baffles are kept at a temperature between −30° and −50° C. A residence section, which is kept at a temperature between 0° and +10° C., is provided between the perforated cooling section and the baffles, in order to make it possible to keep the baffles at a low temperature. The acetic acid still present reacts with the crude ketene in this residence section. Acetic anhydride is formed, which is separated off as such. The gas stream is kept at a velocity of 200 to 2 m/second and a pressure of 50 to 500 mbars. The ketene which emerges is substantially free from mist, but still contains residues of condensable impurities. The disadvantages of this process are an expensive condensation system, which is difficult to clean, and the requirements of very low temperatures and thus a high energy consumption.

Accordingly, the object of the present invention is to provide a process for the preparation of ketene, which makes possible as high a yield of ketene as possible, relative to the acetic acid employed, at a low energy requirement and using simple condensers. This object is achieved by a process for the preparation of ketene, which comprises passing the cracked gas through one or more shell-and-tube heat exchangers arranged in tandem and having a volume V[m$^3$], a pressure drop of 50 to 150 mbars and a surface/volume ratio of 60 to 120 m$^{-1}$, and drawing off the condensate, it being necessary for the quantity of acetic acid employed for the thermal cracking reaction to be 0.5 to 2.5 t×hours$^{-1}$×m$^{-3}$, relative to the volume V of the shell-and-tube heat exchanger.

As already mentioned, the cracked gas also contains solid constituents, such as carbonized material and in some cases ammonium salts, which are precipitated in the condensation system, as a result of which the pressure in the cracking furnace increases and the reaction is adversely affected. For this reason, the condensers have hitherto been given generous dimensions, in the attempt to achieve as long an operating time of the plant as possible. It was surprising and could not have been foreseen that it would be possible, as a result of reducing the volume of the whole condensation system, with a consequent considerable increase in the gas velocity, to decrease the reverse reaction to a large extent and to increase the degree of conversion of the acetic acid, without the condenser system clogging up prematurely. The increase in the pressure drop has no harmful influence on the conversion. Standardized equipment customary in the art can be used in the process according to the invention; complicated special designs are not necessary.

EXAMPLE 3.6 t/hour of acetic acid are vaporized and the vapors are passed into the cracking tube system of a ketene furnace heated by natural gas. After being preheated, triethyl phosphate is added to the acetic acid vapor, as a catalyst. In the subsequent cracking zone the temperature is increased to 700° C. The pressure at the furnace outlet is 358 mbars. Ammonia is added at that point to the hot mixture of gases (cracked gas).

The gas is now passed, by the shortest path, on the tube side, through a series of 5 shell-and-tube heat exchangers. The first two heat exchangers are charged with cooling water; the remaining three are charged with cooling brine at −10° C. The 5 heat exchangers are identical with one another, each 2,500 mm in length, their diameter is 700 mm and they have 290 tubes of internal diameter 25 mm and a total internal surface of 285 m$^2$. The total volume of the condensers, including heads and separators, is 3.5 m$^3$ and the ratio of surface to volume is 81.5 m$^{-1}$.

The series of heat exchangers is inclined at an angle of 5° to the horizontal. The condensate formed is collected in the rear head of each heat exchanger and is drained into a storage tank. A baffle separator is installed between the third and fourth shell-and-tube. The crude ketene leaves the fifth heat exchanger at a temperature of −5° C. and a pressure of 266 mbars. The pressure drop in the condensation system is 358 mbars−266 mbars=92 mbars. The gas velocity is 30−80 m/second.

The following products are obtained: 1.94 t/hour of ketene and 1.46 t/hour of 38% strength aqueous acetic acid. This corresponds to a conversion of 84% of the acetic acid employed, a ketene yield of 92%, relative to the acetic acid reacted, and a ketene yield of 77%, relative to the acetic acid employed.

COMPARISON EXAMPLE

The acetic acid is cracked as indicated in the example, using the quantities quoted in the example. The pressure at the furnace outlet is 175 mbars.

The condensation system comprises a series of 4 heat exchangers, also with gas flow on the tube side. The first two heat exchangers are charged with cooling water; the remaining two are charged with cooling brine at $-10°$ C. The dimensions of the various large shell-and-tube can be seen from the following table.

| Heat exchanger No. | Length, mm | Diameter, mm | Number of tubes | Internal diameter of the tubes | Internal surface area $m^2$ | Volume, including head, $m^3$ | Surface/volume ratio $m^{-1}$ |
|---|---|---|---|---|---|---|---|
| 1 | 812 | 1,600 | 1,247 | 25 | 79 | 2.9 | 27.3 |
| 2 | 1,880 | 1,750 | 1,492 | 25 | 220 | 3.35 | 65.6 |
| 3 | 2,500 | 1,350 | 794 | 25 | 155 | 3.24 | 47.8 |
| 4 | 2,500 | 800 | 353 | 21 | 58 | 0.96 | 60.4 |
| Total | | | | | 512 | 10.45 | 48.97 |

The series of heat exchangers is inclined at an angle of 27° to the horizontal.

The condensate formed is collected in the head and is drained into a storage tank, as indicated in the example. The crude ketene leaves the fourth heat exchanger at a temperature of $-5°$ C. and a pressure of 162 mbars. The pressure drop in the condensation system is therefore 175 mbars$-$162 mbars$=$13 mbars. The gas velocity is 15 to 25 m/second.

1.35 t/hour of ketene and 2.11 t/hour of 70% strength aqueous acetic acid are obtained. This corresponds to a 58% conversion of the acetic acid employed, a ketene yield of 92%, relative to the acetic acid reacted, and a ketene yield of 54%, relative to the acetic acid employed.

We claim:

1. A process for the preparation of ketene by thermal, catalytic cracking of acetic acid under reduced pressure and by cooling the hot cracked gases to substantially 0° C. to $-10°$ C., so that water, unreacted acetic acid and acetic anhydride are condensed, which process comprises passing the cracked gas through at least one shell-and-tube heat exchanger in tandem and having a volume V[$m^3$], a pressure drop of 50 to 150 mbars and a surface/volume ratio of 60 to 120 $m^{-1}$, and drawing off the condensate, wherein the quantity of acetic acid employed for the thermal cracking is at a rate of 0.5 to 2.5 tons per hour per cubic meter, for each cubic meter of the volume V of the at least one shell-and-tube heat exchanger.

2. Process as in claim 1, wherein a succession of several shell-and-tube heat exchangers is employed.

3. Process as in claim 2, wherein said heat exchangers are inclined to the horizontal at an angle of about 5° to about 27°.

4. Process as in claim 1, wherein said surface/volume ratio is of the order 81.5 $m^{-1}$.

* * * * *